United States Patent [19]

Burke

[11] Patent Number: 5,162,649
[45] Date of Patent: Nov. 10, 1992

[54] ION MOBILITY DETECTOR

[75] Inventor: James R. Burke, Shrewsbury, United Kingdom

[73] Assignee: Graseby Ionics Ltd., Watford, United Kingdom

[21] Appl. No.: 582,938

[22] PCT Filed: Mar. 29, 1989

[86] PCT No.: PCT/GB89/00317
§ 371 Date: Dec. 3, 1990
§ 102(e) Date: Dec. 3, 1990

[87] PCT Pub. No.: WO89/09934
PCT Pub. Date: Oct. 19, 1989

[30] Foreign Application Priority Data

Apr. 6, 1988 [GB] United Kingdom ............... 8807994

[51] Int. Cl.⁵ .............................................. H01J 49/40
[52] U.S. Cl. ..................................... 250/287; 250/281
[58] Field of Search ................... 250/287, 281; 422/98

[56] References Cited
U.S. PATENT DOCUMENTS 4,390,784  6/1983  Browning et al. ................. 250/287
4,797,554  1/1989  Blanchard et al. ................ 250/287
4,950,893  8/1990  Reategui et al. .................. 250/282

FOREIGN PATENT DOCUMENTS 2002574  2/1979  United Kingdom ............... 250/287

Primary Examiner—Jack I. Berman
Assistant Examiner—James E. Beyer
Attorney, Agent, or Firm—McAulay Fisher Nissen Goldberg & Kiel

[57] ABSTRACT

An ion mobility detector is disclosed having a drift tube of non-electrically conductive material and a series of spaced conductive rings disposed upon the exterior surface of the tube. An adjustable high voltage source is provided to apply voltages to the rings to establish a potential gradient along the drift tube. The detector further includes a reaction region separated from the drift tube by an injection gate. The ratio of the width of the conductive rings to their thickness is at least 2.1 and the ratio of the internal diameter of the drift tube to the maximum transverse dimension of the injection gate also is at least 2:1.

27 Claims, 2 Drawing Sheets

ION MOBILITY DETECTOR

BACKGROUND OF THE INVENTION

This invention relates to ion mobility detectors and more particularly the ion accelerating structure of such detectors.

Ion mobility detectors are used to detect the presence of unknown materials in an environment, for example contaminants in atmospheric air. A library of known possible contaminants is built up and the measurements known for these are then compared with the results with an unknown species to decide whether a sample contains a contaminant and if so whether it has already been identified. Measurement of concentration or an indication of concentration can be given as well as qualitative identification of the species.

Typical prior art ion mobility detectors have an ionization source, an ion reactant region, an ion drift region, an ion injection shutter or grid interposed between the ion reactant region and the ion drift region, and an ion detector. The systems operate at atmospheric pressure where the mean free path of the contained gas in the drift region is a small fraction of the dimensions of the container. A carrier gas, normally purified atmospheric air (particularly purified to remove water vapour which can interfere with certain types of charged species) is introduced into the ion mobility detector with a gaseous sample of the material whose identity is to be determined by characterization of its ion mobility properties. The carrier gas containing the sample is introduced through an inlet so as to be exposed to the ionization source. This causes portions of both the carrier gas and the sample to be directly ionized at the ionization source. In general, the molecules of the carrier gas are more easily ionized by the ionization source than other molecules of the sample. The gaseous mixture is located within the reactant region at this stage and since the mean free path is many times smaller than the dimensions of the reactor region, multiple collisions between the molecules of the carrier and the sample gas(es) occur, the result of which is that the ion charge tends to be transferred by these collisions from the carrier molecules to the sample molecules thus resulting in a secondary ionization process which ionizes an increased number of the molecules of the sample gas. The reactant region is normally arranged to be under the influence of a potential gradient which moves the charged mixture towards the ion injection grid which is electrically charged to prevent transfer of ions from the reactant region to the drift region but which can be de-energized so as to let a pulse of ions pass through into the drift region. Accordingly, periodically the grid is deionized for a short time and a number of ions are introduced into the drift region. The drift region is arranged to be under the influence of an electrostatic drift field or potential gradient which acts to move ions in the drift region down the tube away from the ion injection grid towards a collector grid which detects the charged ions and is located at the end of the drift region. The time of arrival of each ion at the detector grid relative to the time that the ion injection grid was opened is determined by the mobility of the ion in the nonionized gas occupying the drift region. Heavier ions move more slowly through the drift region and take longer to arrive at the detector than lighter ions. Ions with similar mobilities tend to bunch together and arrive in groups or bunches at the detector region producing a distribution curve and this can be used to characterize the ions, the peak of the curve being the average for that group or bunch of ions thus enabling one to determine the time taken between the opening of the grid and arrival of the group at the detector.

As mentioned above the present invention is concerned particularly with the structure of the drift region.

Commercially available ion mobility detectors are known which have a drift region of tubular configuration constructed of alternating rings of ceramic material and metal, these electrically conductive metal rings being called guard rings. The stack of rings is clamped together and sealed so as to make a gas tight tube. Since it is difficult to ensure a seal between the rings, conventional devices of this type often enclose the stack of rings within an outer sealed envelope. The electrostatic drift field potential gradient is established by connecting adjacent guard rings to each other via a resistor and connecting the end guard rings to the terminals of a voltage source. The conductive rings afford a series of ascending voltage levels and the longitudinal axis of the tube coincides with the longitudinal axis of the electrostatic field which is thus established.

U.S. Pat. No. 4390784 proposes a drift tube consisting of a tube of ceramic or glass or other suitable nonconductive material, coated continuously along its internal surface with a thick film resistor composition. The drift tube is 3.25" long with an internal diameter of 1" and a potential difference of 1500 volts is impressed across the tube. The patentees in U.S. Pat. No. 4390784 anticipated that the inner glass face of the tube afforded by the glass-like surface of the thick film resistor would "cause ions impinging on the overcoat to stick in the ionized state to the overcoat and neutralize and destroy the fields within the drift region". They found that this was not the case, but did not know why and suggested that either the glass-like surface of the thick film resistor was sufficiently conductive the allow the ions impinging on the interior of the tubes to be deionized and thus become ineffective in neutralizing the field or else the ions did stick to the surface but repelled like ions approaching the surface, the net change in the field thus being negligable. They thought it likely that their arrangement was operative because it included elements of both the above possible effects.

U.S. Pat. No. 3522425 discloses a "conventional" voltage divider 50 comprising a plurality of spaced circumferential conductive plates interconnected by resistors 52 and terminally connected to a lead 26 connectable to a battery source and to a grounded electrode 12 so as to provide a relatively uniform field gradient. The specific potential difference utilized in U.S. Pat. No. 3522425 was 625 volts.

GB 2033145A discloses a drift tube in which conductive rings are disposed on the inner surface of a nonconductive housing to establish a linear electric field along the tube. The rings are thicker than they are wide and are spaced apart by distances greater than their width. They are shown as connected by wires passing out through the housing to an external voltage divider network.

SUMMARY OF THE INVENTION

The present invention is concerned with providing a structure which will enable much higher resolution of the charged species to be attained by enabling drift tubes of greater length to be used, thus providing much longer drift times.

We prefer to use a potential gradient in the range 150 to 350 volts per centimeter, desirably from about 225 to 275 e.g. about 250 volts per centimeter. In this voltage range the energy possessed by the ions is essentially that due to their temperature and is referred to as "thermal energy".

In a preferred form of the present invention, the drift tube of an ion mobility detector is provided by a tube of glass or other suitable nonconductive material to the external surface of which is applied a series of spaced conductive rings to which the voltages are applied to establish a potential gradient along the tube.

Thus according to a first aspect of the present invention an ion mobility detector has a drift tube or a reactant tube or both of glass or other non-electrically conductive material with a series of spaced conductive rings disposed upon the exterior surface of the tube or tubes and means for applying voltages to the said rings to establish a potential gradient along the tube or each tube, the ratio of the width of the rings to their thickness being at least 2:1. Contrary to what the patentees of U.S. Pat. No. 4390784 found, we have found that there is a tendency for charged species to stick to the inner surface of the glass tube when the length of the tube alone is increased in order to achieve longer drift times.

Thus when the operative length of the drift tube, namely the length over which the potential gradient is applied is 100 mm or greater, then the internal diameter is desirably in excess of 50 mm, e.g. at least 60, 70, 80 or 90 mm.

Accordingly thus in a preferred form of the invention, the drift tube has a length of at least 100 mm and an internal diameter of at least 50 mm. In a particularly preferred embodiment the drift tube has a length of 500 mm and the internal diameter of 100 mm. The conductive rings may advantageously consist of rings of metal, e.g. copper, foil or tape affixed to the tube by an appropriate adhesive.

The ratio of the width of the rings to their thickness is preferably at least 10:1, e.g. in the range of 2:1 to 100:1.

The ratio of the width of the conductive rings to the spacing between adjacent conductive rings is preferably greater than 1:1, e.g. at least 2:1 and preferably in the range 3:1 to 7:1.

The non-conductive tube is preferably of glass, in particular heat resisting glass, to permit the detector to be heated above ambient temperature during operation.

According to a second aspect of the present invention in an ion mobility detector which has a reaction region and a drift tube separated by an injection gate, the ratio of the internal diameter of the drift tube to the maximum transverse dimension of the injection gate is at least 2:1.

To establish the requisite electric field within the longer drift region necessary for a high resolution detector requires an overall potential difference considerably greater than that necessary for conventional prior art tubes, e.g. of the order of at least 5000 or 10,000 volts and preferably at least 20 Kv.

For considerations of safety, it is preferred that the sample injection end of the tube is arranged to be held at or near earth potential, requiring the collector electrode at the other end of the tube, and the amplifier coupled to it, to be at an elevated negative or positive potential e.g. 20 Kv or more. In a preferred form of the invention the means for recording, indicating or further processing of the signal output of the amplifier are isolated from the elevated voltage. This is preferably achieved by converting the output signal of the amplifier to a light output of intensity proportional to the signal amplitude and linking it e.g. by a fiber optic coupling, to an optical input for the recording, indicating or processing means.

The invention may be put into practice in various ways and one specific embodiment will be described to illustrate the invention with reference to the accompanying diagrammatic representations of which

DETAILED DESCRIPTION

Figure 1:
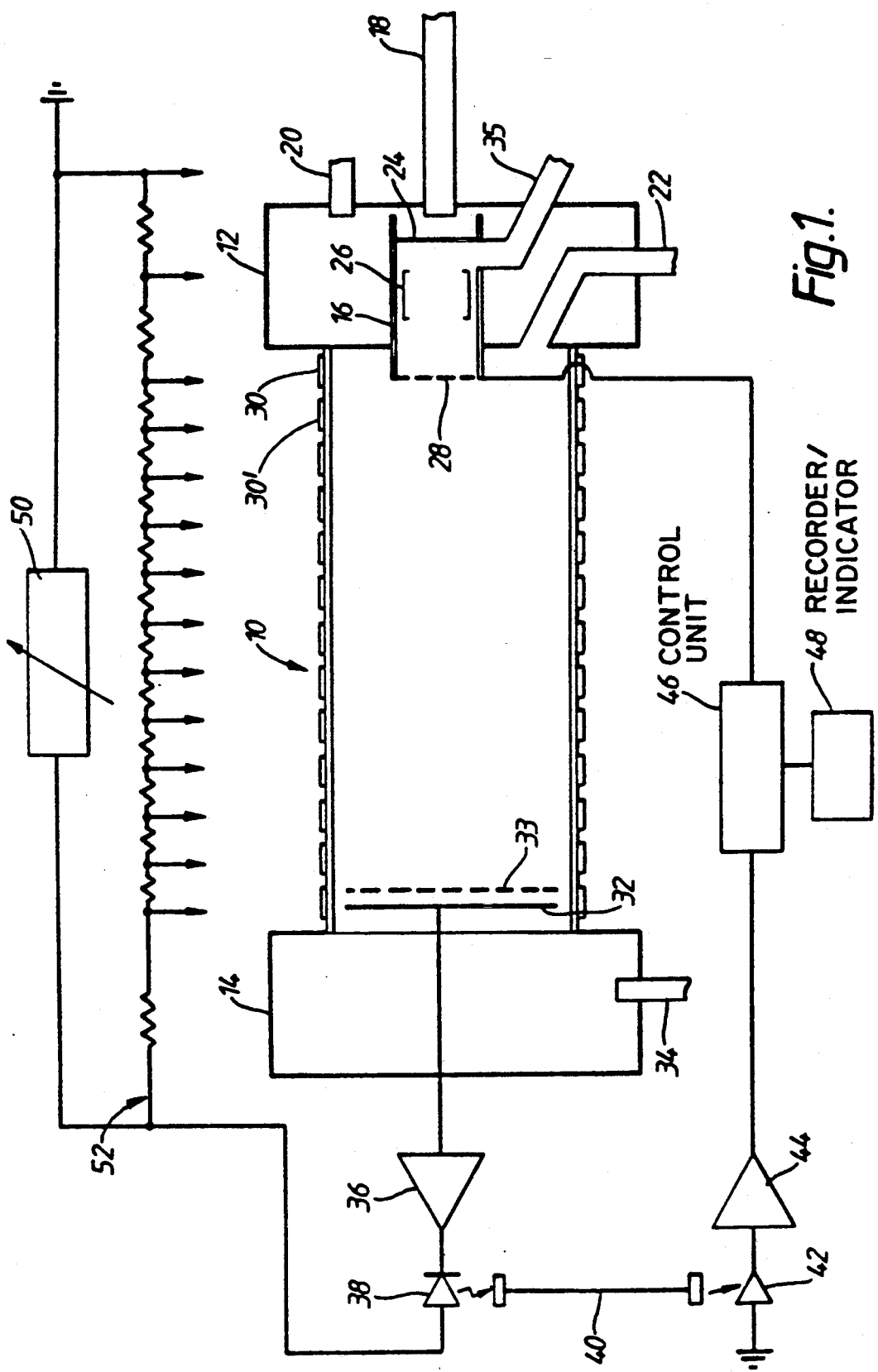
FIG. 1 is a block schematic of an ion mobility detector constructed in accordance with the principles of the invention and FIG. 2 is a side elevation of a detector tube according to the invention.

Referring to FIG. 1 an ion mobility detector comprises a reactant region tube 16 in which molecule-ions of the sample are generated and a drift tube 10 in which the mobilities of the ions generated are determined. The ion drift tube is mounted between two end caps 12 and 14. The end cap 12 carries the reactant region tube 16. An inlet nozzle 18, carried by the end cap, is juxtaposed to one end, the inlet end, of the reaction tube. The end cap 12 also has a vent 20 to atmosphere to enable gases within the cap to be removed e.g. to vent to atmosphere. The reactant region tube 16 is closed at its inlet end by a membrane 24. An ionizing source 26 is disposed within the tube 16. The other end, the outlet end, of the tube 16 is closed by an injector grid 28. The tube 16 is a metal tube. The injector grid 28 is mounted on a ceramic ring which seals against the end of the tube 16 and insulates the grid 28 from the tube. The grid 28 consists of a so-called fixed grid and a so-called moving grid downstream of the fixed grid.

The drift tube is provided with a system for passing a drift gas through it from the end cap 14 to the end cap 12 which thus also carry a drift gas inlet 34 and a drift gas outlet 22 respectively.

The reactant region tube 16 is also provided with an inlet 35 for a carrier gas (which may be the same or different to the drift gas). The drift and carrier gases may be supplied from disposable sources e.g. pressurized cylinders of purified gas in known manner or may be connected to recirculating pumps, purifiers and driers so that the gases are conserved and held pure and of desired dryness, also in known manner.

The end cap 14 also carries a collector electrode 32 mounted within the drift tube 10 and preceeded by a screen grid 33. The screen grid 33 is provided in order to overcome capacitative coupling and it is held at a constant potential relative to the collector such that the potential gradient in the space between the screen grid 33 and the collector electrode 32 is comparable to or greater than that in the rest of the drift tube.

The collector electrode has a diameter about 70% of the internal diameter of the drift tube.

The drift tube 10 is provided with a structure for applying a potential gradient along the length of the tube. This structure consists of a series of spaced apart electrodes $30$–$30^n$ on the drift tube 10 each formed as a continuous conductive ring extending around the tube. The rings are spaced apart along the tube and have an appropriate voltage applied to each ring to establish the desired voltage gradient.

The voltages are applied by means of an adjustable high voltage source shown schematically in FIG. 1 as 50 bridged by a resistor chain again shown schematically as 52 which is connected between the inlet nozzle 18 (which is held at zero potential) and the collector electrode 32 (which is at high positive or negative potential).

Intermediate points on the chain 52 are connected ionizing source 26, the fixed grid of the gate to the ionizing source 26, the fixed grid of the gate 28 and the conductors 30 on the drift tube 10 and to the collector grid 32 and the screen grid 33 and establish appropriate potential differences at these various locations in the detector.

The source 26 is preferably the well known $^{63}$Ni foil radioactive source which produces beta radiation. A linear potential gradient increase is established as described below, from the source 26 to the outlet end of the tube 16, acting to move the charged ions from the vicinity of the source to the injector grid 28 where if the gate is closed the ions are discharged. This movement reduces loss of ions due to recombination.

The potential steps between the conductors 30 of the drift tube are equal.

The ion drift tube 10 is a glass tube which carries on its outer surface a series of discrete electrodes $30'$, $30^2$, $30^3$ to $30^n$. In this specific embodiment n is 36.

The collector electrode 32 is connected to an amplifier 36 which has an optical diode 38 at its output, this diode is run at the same potential as the collector grid 32. A fiber optic link 40 couples the light output of the diode 38 to the input of a diode 42 at the input of an amplifier 44, the output of which is connected to the input of an electronic control unit 46. The control unit supplies an output to recorder/indicator 48 and is arranged to provide a trigger pulse to the injector grid 28.

The injector grid 28 is normally biased electrically by the control unit 46 to prevent the passage of ions, but periodically is gated by means of an electrical pulse from the control unit 46 to permit the injector grid 28 to pass a pulse of ions into the drift tube 10.

The grid 28 is typically two sets of parallel, almost interdigitated wires. The grid is closed when a potential difference is applied between the two sets of wires. When there is no potential difference between the two sets of wires, e.g. when they are connected electrically, ions can flow through the grid. The grid affords a circular opening to the drift tube, the opening having a diameter of 12 mms.

Figure 2:
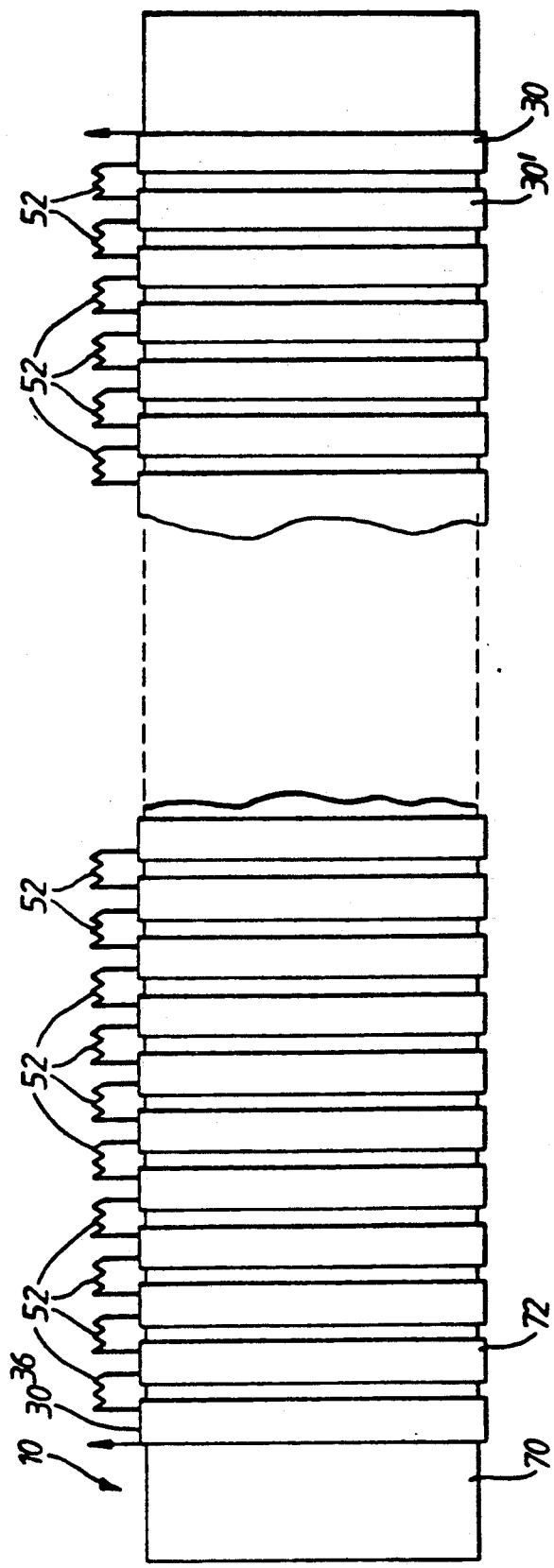

Referring to FIG. 2, the ion drift tube 10 is constructed of a preformed glass tube 70 bearing a series of electrodes 30, $30^1$, $30^2$–$30^n$ (n being 36) each formed as a continuous conductive ring 72 around the tube 70.

In a modified arrangement (not shown) the tube 16 could be constructed in the same way. It would be shorter and narrower than the tube 10 and have fewer electrodes.

The rings 72 are conveniently of copper foil in the form of a copper shielding tape coated on one side with a thermosetting acrylic adhesive enabling the tape to be mounted upon tube 70.

The potential difference across the resistor chain from 18 to 32 is 20 Kv. The potential of the source 26 is 470 volts and it is spaced about 4 mms from the fixed grid which is held at 670 volts. Thus the field gradient is at least as much as in the tube 10 (which is 250 volts/cm) and desirably slightly higher. The moving grid of the injector grid 28 is held at a voltage above that of the fixed grid by the controller 46 e.g. 30, 40 or say 70 volts to hold the injection gate 28 closed. The controller equalizes the voltages to open the gate. The resistors between the conductors 30 are each 10 megohms producing a potential difference from 740 volts at conductor 30 to 20 Kv at conductor $30^{36}$. The values of the resistors 30 are kept very closely similar to maintain an even electrostatic field. This is a considerable advantage over the thick film resistor concept of U.S. Pat. No. 4390784 where it is difficult to avoid variations in film thickness and thus resistance which distorts the electrostatic field.

The operation of the device is as follows. Drift tube gas, typically dried purified air or nitrogen, is circulated through the drift tube 10 entering at 34 and exiting at 22. Conventional flow rates known in the art are used e.g. 1 to 30 ccs of gas per cc of drift tube volume/minute.

The air is desirably zero air (i.e. 2.0 ppm hydrocarbons as $CH_4$ maximum). The nitrogen is desirably at least 99.998% pure. The function of the drift gas is to quench ion-molecule reaction in the drift tube.

The carrier gas which in a typical use is ambient atmospheric air containing a gas sample to be detected and characterized is drawn in to the inlet 18 by means of a pump attached to the vent 20. Similar low rates in relation to the volume of the reactant tube may be used as for the drift gas. The membrane 24 is chosen to be selectively permeable to species which it is wished to detect such as organic molecules, whilst being much less permeable or essentially impermeable to $H_2O$, $O_2$, $N_2$ and $CO_2$. The species it is wished to detect thus permeate through the membrane into the reactant tube 16 together with some of the carrier gas into the vicinity of the ionizing source 26. The membrane may comprise a sheet of silicone-based rubber material such as dimethyl silicone rubber. The voltages source is switched on and thus the carrier gas molecules are ionized and to a lesser extent the sample species.

As the ion mobility detector operates at or near atmospheric pressure, the mean free path of the ions and other molecules is small in relation to the dimensions of the confining space and there are many collisions between the various gas molecules in the reactant region within tube 16. The collisions tend to produce ionized sample molecules and deionize previously ionized carrier gas molecules.

The field potential gradient in tube 16 between the inlet nozzle 18 and the ionizing source 26 moves the ions generated by the radiation source from the carrier and sample gas towards the injector grid 28.

The ion mobility detector can detect either positively charged or negatively charged ions. If the potential at the collector grid 32 is positive then negative ions will be attracted towards it and vice versa. Let us assume that the collector grid 32 is positive, the negative ions continuously generated in the reactant tube are moved towards the grid 28 by the potential difference between the grid 28 and the source 26 and are discharged when they reach the grid 28 if it is closed. The positive ions generated in the tube 16 move towards the inlet end of the tube and are discharged.

$^{63}$Ni beta radiation produces negative sample ions via free thermal electrons which attach to oxygen molecules as they drift down the reaction tube and undergo a stabilizing collision with a third body e.g. a sample molecule (M) as $e + O_2 + M = O_2^- + M$.

When an $O_2^-$ ion collides with a sample molecule M a charge exchange occurs producing a charged sample molecule as $$O_2^- + M = O_2 + M^-.$$

It is these $M^-$ ions which are drawn down the tube to the grid 28.

The grid typically is opened, by the controller 46 removing the potential, for about 0.18 milliseconds (ms) every 18 ms thus introducing a regular pulse or slice of negatively charged ions into the drift tube 10. This time interval of 18 ms is known as the cycle time. As is well known in the art the cycle time can be varied as desired e.g. between 18 and 640 ms. As mentioned above the counterflowing drift tube gas has the function of quenching any further reactions between the ions.

The ions then are moved down the tube by the applied very even electrostatic field to the collector 32 and as they pass down the tube 10 they separate into faster smaller ions followed by slower larger ions and each group or cluster arrives at the electrode as a distribution around a mean or peak which is used to identify the mobility of the particular ion species. The ions thus tend to become bunched into discrete mobility groups, the bunches or clusters reaching the collector electrode 32 at discrete times after their injection into the drift tube by the injector grid 28, the drift times being directly related to ion mobilities.

The ions are deionized by the collector electrode 32 and this generates an electrical current at the input to the amplifier 36 related to the number of ions in each bunch as it strikes the electrode 32.

The current is amplified by the amplifier 36 producing related variations in the intensity of the light emitted by the light emitting diode 38.

The emitted light is coupled by the fiber-optic coupling 40 to the diode 42 which generates a related current at the input of the amplifier 44, which is amplified and passed through the control unit 46 to the indicator/recorder 48, which may be an oscilloscope or pen recorder or both.

The construction, circuitry and mode of operation of the controller 46 are those conventionally used for ion mobility detectors.

The current signal from the electronic control unit 46 to the indicator/recorder 48 is an ion mobility spectrum which can be calibrated in ion mobility and related to the quantity and type of samples present in the atmosphere sampled by the inlet nozzle 18.

The flow of drift gas through the tube 10 serves to remove non-ionized molecules of sample and carrier which may have passed through the injector electrode 28 and which could, if not removed, be ionised by collision at a time later than injection of the original sample ions, thus broadening the ion mobility spectra.

Some sample materials ionize into a single ion species, others into a number of ion species. The time of arrival and size of these peaks can be used as a characteristic spectrum by which an unknown species can be correlated with a known sample, provided that the drift conditions are the same i.e. potential, carrier gas, value, purity, pressure and humidity.

The controller 46 preferably thus contains a library of spectra for known species. These can be displayed on the recorder-display 48 and compared with the unknown sample or the comparison can be done in the controller and when a fit is detected the name of the detected species then displayed.

In addition the concentration of the detected species can be measured and a direct numerical read out or merely an indication of concentration levels given.

As indicated above the grid 28 is pulsed every cycle which as mentioned above is 18 ms. The collector electrode 32 whose time constant may be greater than the cycle time measures the ion peak pattern continuously, the amplitude of the pulse being proportional to the number of ions, the ion arrival time being characteristic of the ion. Thus the actual drift time of the ion is the time base and a complete ion drift pattern is generated in each cycle. It can take a few seconds for the sample to clear the cell thus averaging repetitive scans over a number of cycles can help obtain an improved signal to noise ratio.

We have found however that with conventional relatively narrow diameter drift tubes when the length of the tube is increased the peaks tend with time to drift to longer drift times and to reduce in amplitude. We have found that this problem can be avoided by using a tube which is at least 100 mm in internal diameter when the tube length is 500 mm; or more broadly for tubes of 100 mms length or more the internal diameter should be at least 50 mm. Put another way the ratio of the internal diameter of the drift tube 10 to the diameter of the injection gate 28, which may be the same as, greater or smaller than the internal diameter of the reaction tube 16, should be at least 2:1 preferably at least 3:1, for example in the range 3:1 to 15:1 or 5:1 to 10:1 especially about 8:1.

In an ion mobility detector in accordance with the invention the tube 10 was 500 mm long with an internal diameter of 100 mm and a wall thickness of 6 mm. The material used was pre-formed tubular stock of PYREX heat resistant glass. Copper tape used to form electrodes 30, $30^1$... was 10 mm wide and about 0.5 mms thick. More broadly thicknesses in the range 0.1 to 1,2,3,4 or 5 mms may be useful the range 0.1 to 1 mms being preferred. The ratio of tape width to thickness should thus be at least 2:1 e.g. at least 10:1 and can thus be in the range 100:1 to 2:1 e.g. 50:1 to 5:1 preferably about 40:1 to 10:1 especially about 20:1. Thirty six electrodes were mounted on the tube separated by 2 mm gaps. The ratio of the width of the conductive rings to the spacing between adjacent conductive rings is preferably greater than 1:1 e.g. at least 2:1 or 3:1, 4:1 or 5:1 or 10:1. A preferred ratio is about 5:1 e.g. 3:1 to 7:1.

The potential difference impressed across the drift tube 10 was adjustable between 10 kV and 26 kV to vary the drift field within the tube 10 and hence the resolution of the detector.

The resolution of the detector is defined in this context as the time-of-flight of an ion species divided by the full width (in time) of the resultant peak at the half-height point.

For the instrument with the dimensions given a resolution of between 100 and 200 was attained for the potential differences quoted.

The structure of the drift tube in accordance with the present invention thus has the advantage that it can readily be made with only narrow spacings between adjacent conductors namely only 20% of the conductor width as compared to in excess of 100% in the conventional alternating ring structures known in the prior art. This results in improved field uniformity. Moreover with the conventional alternating ring stacked structure, if one wants to increase the length of the tube it becomes unmanageably heavy and mechanically increasingly difficult to clamp the rings and keep the tube straight, and as mentioned above recourse is often made to an external envelope to ensure adequate sealing, such a requirement adds to the complexity and cost of the device.

I claim:

1. In an ion mobility detector having a reaction region and a drift tube separated by an injection gate, wherein the improvement comprises:
the ratio of the internal diameter of said drift tube to the maximum transverse dimension of said injection gate being at least 2:1.

2. An ion mobility detector comprising:
a drift tube of non-electrically conductive material;
a series of spaced conductive rings disposed upon the exterior surface of said tube;
means for applying voltages to said rings to establish a potential gradient along said tube, the ratio of the width of said rings to their thickness being at least 2:1;
a reaction region; and
an injection gate separating said drift tube from said reaction region, the ratio of the internal diameter of said tube to the maximum transverse dimension of said gate being at least 2:1.

3. An ion mobility detector as claimed in claim 2, wherein said conductive rings are metal foil affixed to said tube.

4. An ion mobility detector as claimed in claim 2, wherein the ratio of the width of said conductive rings to the spacing between adjacent conductive rings is greater than 1:1.

5. An ion mobility detector as claimed in claim 2, wherein the ratio of the width of said conductive rings to the spacing between adjacent conductive rings is at least 2:1.

6. An ion mobility detector as claimed in claim 2, wherein the ratio of the width of said conductive rings to the spacing between adjacent conductive rings is in the range from about 3:1 to 7:1.

7. An ion mobility detector as claimed in claim 2, wherein said drift tube is made of glass.

8. An ion mobility detector as claimed in claim 2, wherein said conductive rings are metal tape affixed to said tube.

9. An ion mobility detector comprising:
a drift tube made of non-electrically conductive material;
a series of spaced conductive rings affixed to the exterior surface of said tube;
means for applying voltages to said rings to establish a potential gradient along said tube, the ratio of the width of said rings to their thickness being at least 10:1;
the operative length of said tube over which the potential gradient is applied being at least 100 mm and the internal diameter of said tube being at least 50 mm;
a reaction region;
an injection gate separating said drift tube from said reaction region;
the ratio of the internal diameter of said tube to the maximum transverse dimension of said gate being at least 2:1; and
the ratio of the width of the conductive rings to the spacing between adjacent conductive rings being greater than 1:1.

10. An ion mobility detector as claimed in claim 9, wherein the ratio of the width of the rings to their thickness is in the range from about 2:1 to 100:1.

11. An ion mobility detector as claimed in claim 9, wherein the ratio of the width of the conductive rings to the spacing between adjacent conductive rings is at least 2:1.

12. An ion mobility detector as claimed in claim 9, wherein the ratio of the width of the conductive rings to the spacing between adjacent conductive rings is in the range from about 3:1 to 7:1.

13. An ion mobility detector as claimed in claim 9, wherein said tube is made of glass and said conductive rings are made of metallic material.

14. An ion mobility detector comprising:
a drift tube of non-electrically conductive material;
a series of spaced conductive rings disposed upon the exterior surface of said tube;
means for applying voltages to said rings to establish a potential gradient along said tube, the ratio of the width of said rings to their thickness being at least 2:1.
the operative length of said tube over which the potential gradient is applied being at least 100 mm and the internal diameter of said tube being at least 50 mm;
a reaction region; and
an injection gate separating said drift tube from said reaction region, the ratio of the internal diameter of said tube to the maximum transverse dimension of said gate being at least 2:1.

15. An ion mobility detector as claimed in claim 1, wherein the ratio of the width of said rings to their thickness is at least 10:1.

16. An ion mobility detector as claimed in claim 1, wherein the ratio of the width of said rings to their thickness is in the range from about 2:1 to 100:1.

17. An ion mobility detector as claimed in claim 14, wherein the ratio of the width of said conductive rings to the spacing between adjacent conductive rings is greater than 1:1.

18. An ion mobility detector as claimed in claim 14, wherein the ratio of the width of said conductive rings to the spacing between adjacent conductive rings is at least 2:1.

19. An ion mobility detector as claimed in claim 14, wherein the ratio of the width of said conductive rings to the spacing between adjacent conductive rings is in the range from about 3:1 to 7:1.

20. An ion mobility detector comprising:
a drift tube of non-electrically conductive material;
a series of spaced conductive rings disposed upon the exterior surface of said tube;
means for applying voltages to said rings to establish a potential gradient along said tube, the ratio of the width of said rings to their thickness being at least 10:1;
a reaction region; and
an injection gate separating said drift tube from said reaction region, the ratio of the internal diameter of said tube to the maximum transverse dimension of said gate being at least 2:1.

21. An ion mobility detector as claimed in claim 20, wherein the ratio of the width of said conductive rings to the spacing between adjacent conductive rings is greater than 1:1.

22. An ion mobility detector as claimed in claim 20, wherein the ratio of the width of said conductive rings to the spacing between adjacent conductive rings is at least 2:1.

23. An ion mobility detector as claimed in claim 20, wherein the ratio of the width of said conductive rings to the spacing between adjacent conductive rings is in the range from about 3:1 to 7:1.

24. An ion mobility detector comprising:
a drift tube of non-electrically conductive material;
a series of spaced conductive rings disposed upon the exterior surface of said tube;
means for applying voltages to said rings to establish a potential gradient along said tube, the ratio of the width of said rings to their thickness is in the range from about 2:1 to 100:1;
a reaction region; and
an injection gate separating said drift tube from said reaction region, the ratio of the internal diameter of said tube to the maximum transverse dimension of said gate being at least 2:1.

25. An ion mobility detector as claimed in claim 24, wherein the ratio of the width of said conductive rings to the spacing between adjacent conductive rings is greater than 1:1.

26. An ion mobility detector as claimed in claim 24, wherein the ratio of the width of said conductive rings to the spacing between adjacent conductive rings is at least 2:1.

27. An ion mobility detector as claimed in claim 24, wherein the ratio of the width of said conductive rings to the spacing between adjacent conductive rings is in the range from about 3:1 to 7:1.

* * * * *